United States Patent [19]
Maekawa et al.

[11] Patent Number: 5,981,764
[45] Date of Patent: Nov. 9, 1999

[54] PROCESS FOR PRODUCING 1-AMINOPYRROLIDINE, AND 1-AMINOPYRROLIDINE ACCORDING TO THE PROCESS

[75] Inventors: Tsukasa Maekawa; Yoshihisa Tomotaki; Keiichiro Ishikawa; Akihiro Nabeshima; Tomohiro Furuichi, all of Tokushima, Japan

[73] Assignee: Otsuka Chemical Co., Ltd., Osaka, Japan

[21] Appl. No.: 09/121,599

[22] Filed: Jul. 24, 1998

[30] Foreign Application Priority Data

Jul. 25, 1997 [JP] Japan .................................. 9-200115

[51] Int. Cl.$^6$ .................................................. C07D 207/50
[52] U.S. Cl. ............................................................. 548/557
[58] Field of Search ............................................... 548/557

[56] References Cited

U.S. PATENT DOCUMENTS 4,564,677  1/1986  Kantor ..................................... 544/164
5,514,505  5/1996  Limburg et al. ......................... 430/41

FOREIGN PATENT DOCUMENTS 0 850 930 A2  7/1998  European Pat. Off. .
07179421  3/1995  Japan .

OTHER PUBLICATIONS

Jain, S.R., et al. "Syntheses of some N–substituted hydrazines by the anhydrous chloramine process," *Proceedings of the Indian Academy of Sciences* (*Chemical Sciences*), vol. 95, No. 4, Oct. 1985, pp. 381–389.

Reinbol'd, A. M., et al., "Preparation of 1-aminopyrrolidine," *Chemical Abstracts*, Vo. 112, No. 21, May 21, 1990, XP–002084391.

Hioki, T., et al., "Preparation of bipyrrolidine and analogs," *Chemical Abstracts*, vol. 123, No. 23, Dec. 4, 1995, XP–002084927.

*Primary Examiner*—Johann Richter
*Assistant Examiner*—Dominic Keating
*Attorney, Agent, or Firm*—Whitham, Curtis & Whitham

[57] ABSTRACT

1-Aminopyrrolidine which is obtained by reacting hydrazine hydrate with a compound represented by the following formula (I):

$$X^1-C_4H_8-X^2 \qquad (I)$$

wherein $X^1$ and $X^2$ are the same or different, and each represents a leaving group, in methanol; and a process for producing 1-aminopyrrolidine, comprising the step of reacting hydrazine hydrate with the above compound represented by formula (I) in methanol.

3 Claims, No Drawings

PROCESS FOR PRODUCING 1-AMINOPYRROLIDINE, AND 1-AMINOPYRROLIDINE ACCORDING TO THE PROCESS

BACKGROUND OF THE INVENTION

1. Field of the Invention

The present invention relates to a process for producing 1-aminopyrrolidine, and also to 1-aminopyrrolidine which is produced by the process.

2. Discussion of the Background

1-Aminopyrrolidine is a useful compound as a starting material or synthetic intermediate for tetrahydropyridazine derivatives used as herbicides. 1-Aminopyrrolidine is also a useful compound as a reducing agent, a deoxidizer, a scale inhibitor, an epoxy hardener, or the like.

With regard to the production process of 1-aminopyrrolidine, a process in which hydrazine hydrate is dissolved in isopropanol and then 1,4-dihalobutane and alkali are added thereto under heating is known (see SU 1525151-A1). However, the yield and purity of 1-aminopyrrolidine obtained by the process are not satisfactory.

Additionally, since isopropanol used in the process forms an azeotropic mixture with water in the reaction system, an anhydrous state is resulted in the reaction system during the reaction upon heating and, therefore, it is unavoidable that hydrazine hydrate used as a starting material changes to very toxic and dangerous anhydrous hydrazine whereby there is a problem in the operation.

Moreover, a small amount of isopropanol remains in the crude reaction product together with 1-aminopyrrolidine and fractionation of isopropanol from 1-aminopyrrolidine is very difficult whereby it is unavoidable that yield and purity of the desired product further decrease.

SUMMARY OF THE INVENTION

An object of the present invention is to provide 1-aminopyrrolidine of a high purity, and also to offer a process in which 1-aminopyrrolidine can be produced in a high yield and in a high purity, without danger in the operations but with safety and in an industrially advantageous manner.

This and other objects of the present invention have been accomplished by 1-aminopyrrolidine which is obtained by reacting hydrazine hydrate with a compound represented by the following formula (I):

$$X^1—C_4H_8—X^2 \qquad (I)$$

wherein $X^1$ and $X^2$ are the same or different, and each represents a leaving group (hereinafter referred to as "disubstituted butane"), in methanol.

Furthermore, this and other objects of the present invention have been accomplished by a process for producing 1-aminopyrrolidine, comprising the step of reacting hydrazine hydrate with the above disubstituted butane in methanol.

DETAILED DESCRIPTION OF THE INVENTION

The present inventors have conducted an intensive investigation for solving the above-mentioned problems and, as a result, have found an excellent manufacturing process whereby the present invention has been achieved.

In accordance with the present invention, it is now possible to produce 1-aminopyrrolidine in a yield of 90% or more and in a purity of almost 100%.

Examples of the leaving group (eliminating group) include a halogen atom, a $C_{1-6}$ alkylsulfonyl group, a toluenesulfonyl group, and a group of $—OP(=O)(OR^1)(OR^2)$, in which $R^1$ and $R^2$ are the same or different, and each represents a $C_{1-6}$ alkyl group or a phenyl group.

It is preferred in the present invention that the disubstituted butane is continuously added to hydrazine hydrate while adjusting the pH of the reaction to 8 or higher, preferably 8 to 11. At that time, alkali may be added simultaneously, if necessary.

Example of the disubstituted butane include various ones which have been already known. Specific examples include 1,4-dichlorobutane, 1,4-dibromobutane, 1,4-difluorobutane, 1,4-diiodobutane, 1,4-bis(methyl-sulfonyl)butane, 1,4-bis(p-toluenesulfonyl)butane, and $H_3COP(=O)(OCH_3)O(CH_2)_4OP(=O)(OCH_3)OCH_3$.

The ratio of hydrazine hydrate to the disubstituted butane is not particularly limited; however, usually, the hydrazine hydrate is used in an amount of about 1 to 10 moles per mole of the disubstituted butane. Preferably, if no alkali is used, the former is used in an amount of about 2 to 5 moles per mole of the latter; and if alkali is used, the former is used in an amount of about 1 to 1.5 moles per mole of the latter.

The alkali which can be used in the present invention is not particularly limited. Examples include alkali hydroxides (for example, sodium hydroxide, potassium hydroxide) and alkali carbonates (for example, sodium carbonate, potassium carbonate). If alkali is used, the amount used thereof is not particularly limited; however, usually, the alkali is used in an amount of about 1 to 20 moles, preferably about 2 to 3 moles, per mole of the disubstituted butane.

In the process of the present invention, the pH of the reaction system lowers due to generation of an acid as the reaction proceeds. Accordingly, the reaction may stop so that a sufficiently high yield may not be achieved unless hydrazine hydrate is kept in an excessive amount or unless alkali is added thereto. Therefore, it is preferred in the present invention that the amount of hydrazine hydrate is kept excessively or that alkali which is less than the amount of the generated acid is continuously added whereby the pH of the reaction is maintained within the above-mentioned range.

If hydrazine hydrate is used excessively, unreacted hydrazine hydrate can be extracted, separated and recycled.

The process of the present invention is conducted in methanol as a solvent, preferably under refluxing. The amount used of methanol is not particularly limited; however, usually, methanol is used in an amount of 50 to 200 parts by weight, preferably 70 to 150 parts by weight, based on 100 parts by weight of hydrazine hydrate.

As a result of the use of methanol in the present invention as a solvent, the anhydrous state is not resulted in the reaction system during the heating reaction and, therefore, hydrazine hydrate used as a starting material does not change to toxic and dangerous anhydrous hydrazine and there is no disadvantage in actual operations.

The process of the present invention is usually conducted at room temperature to about 95° C., preferably about 50 to 80° C., for about 1 to 10 hours, preferably about 1 to 3 hours.

1-Aminopyrrolidine obtained according to the process of the present invention can be easily isolated and purified from the reaction mixture by known means such as fractional distillation. For example, methanol can be fractionally distilled from 1-aminopyrrolidine easily and, therefore, it is possible to produce 1-aminopyrrolidine in a high yield and a high purity by means of fractional distillation.

EXAMPLES

The present invention will be further illustrated by way of the following examples. However, the present invention is not limited thereto.

Example 1

A 80% hydrazine hydrate (75 g.; 1.2 mol) and 75 g of methanol were mixed and the temperature in the reaction system (refluxing system) was kept at 70 to 75° C. Into this system, 127 g (1.0 mol) of 1,4-dichlorobutane was added dropwise gradually. According to the addition dropwise, the reaction of 1,4-dichlorobutane with hydrazine hydrate took place whereupon 1-aminopyrrolidine and hydrochloric acid were produced and the pH was lowered. Accordingly, 127 g of 48% aqueous solution of sodium hydroxide was added dropwise thereinto so that the pH of the system did not become lower than 8. When the aqueous solution of sodium hydroxide was added dropwise at such a rate that the pH of the system became higher than 11, 1,4-dichlorobutane was hydrolyzed whereby 1,4-butanediol and 4-chlorobutanol were by-produced and, therefore, the aqueous solution of sodium hydroxide was added dropwise in such a rate that the pH 8 to 11 of the system was maintained. Time required for the addition dropwise was two hours. After completion of the addition, the mixture was stirred at the same temperature for one hour to complete the reaction. The resulting reaction mixture was fractionally distilled to give 82.6 g (yield: 96%) of 1-aminopyrrolidine.

Example 2

A 80% hydrazine hydrate (75 g; 1.2 mol) and 75 g of methanol were mixed and the temperature in the reaction system (refluxing system) was kept at 70 to 75° C. Into this system was added dropwise gradually 46 g (0.36 mol) of 1,4-dichlorobutane during two hours. After completion of the addition dropwise, the mixture was allowed to react under refluxing for three hours. The pH upon completion of the reaction was about 9.0. After methanol was recovered by evaporation, toluene was added to the residue and 1-aminopyrrolidine was continuously extracted to the organic layer to separate from hydrazine hydrate remaining in an aqueous layer. Water was added to the organic layer so that 1-aminopyrrolidine was back-extracted followed by subjecting to fractional distillation to give 28 g (yield: 90%) of 1-aminopyrrolidine. Also, hydrazine hydrate which was extracted and separated therefrom was distilled and recycled.

Example 3

A 80% hydrazine hydrate (75 g; 1.2 mol) and 75 g of methanol were mixed and the temperature in the reaction system (refluxing system) was kept at 70 to 75° C. Into this system was added dropwise gradually 30 g (0.24 mol) of 1,4-dichlorobutane during two hours. After completion of the addition dropwise, the reaction was conducted for three hours under refluxing. The pH after the reaction was 11.0. The same after-treatment as in Example 2 was conducted to give 20 g (yield: 98%) of 1-aminopyrrolidine.

While the invention has been described in detail and with reference to specific embodiments thereof, it will be apparent to one skilled in the art that various changes and modifications can be made therein without departing from the spirit and scope thereof.

This application is based on Japanese application No. Hei 9-200115 filed on Jul. 25, 1997, the entire content of which is incorporated hereinto by reference.

What is claimed is:

1. A process for producing 1-aminopyrrolidine, comprising the step of reacting hydrazine hydrate with a compound represented by the following formula:

$$X^1\text{—}C_4H_8\text{—}X^2 \qquad (I)$$

wherein $X^1$ and $X^2$ are the same or different, and each represents a leaving group, in methanol at a pH of 8 to 11 and at a temperature of 50 to degrees C.

2. The process according to claim 1, wherein said reaction is conducted in the presence of alkali.

3. The process according to claim 1, wherein the leaving group is selected from the group consisting of a halogen atom, a $C_{1-6}$ alkylsulfonyl group, a toluenesulfonyl group, and a group of —OP(=O)(OR$^1$)(OR$^2$), in which $R^1$ and $R^2$ are the same or different, and each represents a $C_{1-6}$ alkyl group or a phenyl group.

* * * * *